United States Patent
Gurfinkel et al.

(10) Patent No.: US 10,018,564 B2
(45) Date of Patent: Jul. 10, 2018

(54) REAGENT-FREE IDENTIFICATION OF BACTERIA CONTAINING RESISTANCE GENES USING A RAPID INTRINSIC FLUORESCENCE METHOD

(71) Applicant: POCARED Diagnostics LTD., Rehovot (IL)

(72) Inventors: Jonathan Gurfinkel, Omer (IL); Gal Ingber, Oranit (IL)

(73) Assignee: POCARED DIAGNOSTICS LTD., Rehovot (IL)

(*) Notice: Subject to any disclaimer, the term of this patent is extended or adjusted under 35 U.S.C. 154(b) by 0 days.

(21) Appl. No.: 15/060,703

(22) Filed: Mar. 4, 2016

(65) Prior Publication Data
US 2017/0023480 A1 Jan. 26, 2017

Related U.S. Application Data

(60) Provisional application No. 62/129,530, filed on Mar. 6, 2015.

(51) Int. Cl.
*G01N 21/64* (2006.01)
*C12Q 1/04* (2006.01)
*G01N 33/483* (2006.01)

(52) U.S. Cl.
CPC ........... *G01N 21/6486* (2013.01); *C12Q 1/04* (2013.01); *G01N 33/4833* (2013.01); *G01N 2021/6417* (2013.01); *G01N 2201/062* (2013.01)

(58) Field of Classification Search
None
See application file for complete search history.

(56) References Cited

U.S. PATENT DOCUMENTS

| | | | |
|---|---|---|---|
| 8,309,897 B2 | 11/2012 | Ingber | |
| 8,519,358 B2 | 8/2013 | Ingber et al. | |
| 8,609,364 B2 * | 12/2013 | Walsh | C12Q 1/025 435/29 |
| 8,804,114 B2 | 8/2014 | Ingber | |
| 8,808,649 B2 | 8/2014 | Ingber et al. | |
| 2006/0141636 A1 * | 6/2006 | Steggles | C12M 33/14 436/177 |
| 2007/0037135 A1 | 2/2007 | Barnes et al. | |
| 2008/0220465 A1 | 9/2008 | Ingber et al. | |
| 2011/0093207 A1 | 4/2011 | Ingber et al. | |
| 2011/0178721 A1 | 7/2011 | Ben-David et al. | |
| 2012/0105837 A1 * | 5/2012 | Ingber | G01N 21/6452 356/246 |
| 2012/0196271 A1 | 8/2012 | Ingber | |
| 2014/0246389 A1 | 9/2014 | Ingber | |
| 2015/0152467 A1 | 6/2015 | Ingber et al. | |

OTHER PUBLICATIONS

Walsh, J.D. et al.,: "Rapid Intrinsic Fluorescence Method for Direct Identification of Pathogens in Blood Cultures", MBio, vol. 4, No. 6, pp. 1-9.

* cited by examiner

*Primary Examiner* — Oluwatosin A Ogunbiyi
(74) *Attorney, Agent, or Firm* — The Webb Law Firm

(57) ABSTRACT

This invention relates to a method that allows for the differentiation of isolates of commonly encountered bacteria that contain specific antibiotic-resistance genes from similar isolates that do not harbor the gene. More particularly, the invention relates to a method that utilizes an automated rapid platform system that employs intrinsic fluorescence, optical data analysis, and artificial intelligence methods to analyze multi-dimensional optical characteristics of bacterial strains.

17 Claims, 1 Drawing Sheet

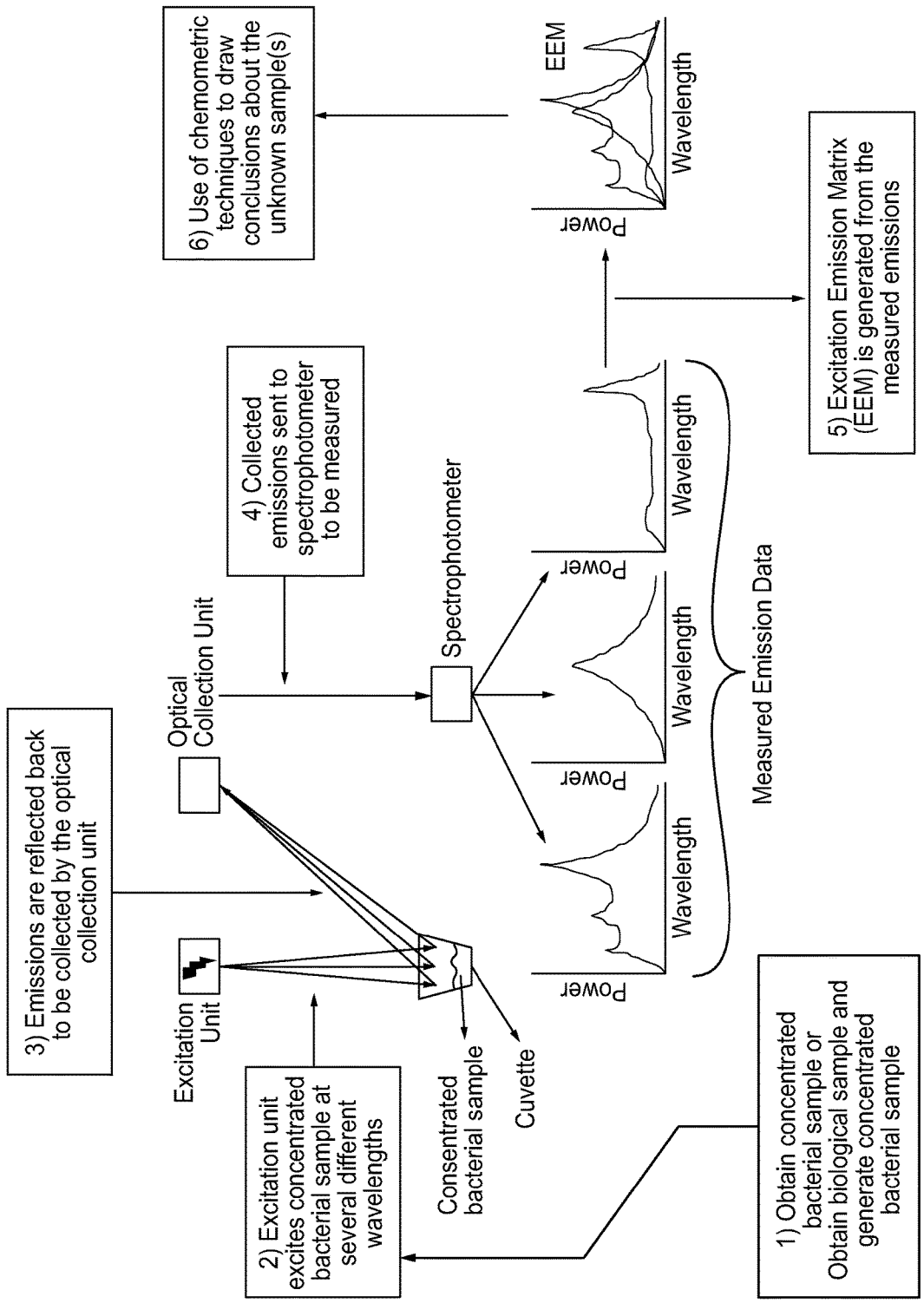

REAGENT-FREE IDENTIFICATION OF BACTERIA CONTAINING RESISTANCE GENES USING A RAPID INTRINSIC FLUORESCENCE METHOD

CROSS REFERENCE TO RELATED APPLICATIONS

This application claims the benefit of U.S. Provisional Patent Application No. 62/129,530 entitled "Reagent-Free Identification of Bacteria Containing Resistance Genes Using a Rapid Intrinsic Fluorescence Method" filed Mar. 6, 2015, which is hereby incorporated by reference in its entirety.

BACKGROUND OF THE INVENTION

Field of the Invention

This invention relates to a method that allows for the differentiation of commonly encountered bacterial isolates that contain specific antibiotic-resistance genes from similar bacterial isolates that do not harbor the antibiotic-resistance gene. Additionally, this invention relates to methods that allow for the differentiation between bacterial strains containing different antibiotic-resistance genes. More particularly, the invention relates to a method for identifying and differentiating bacterial strains, including: 1) obtaining a biological sample, such as blood, urine, and/or any other bodily fluids; 2) processing the biological sample in order to concentrate the bacteria in the biological sample; and 3) running the concentrated bacterial sample through an optical analyzer to obtain intrinsic fluorescence data, which can then be used to determine not only the bacterial strain, but also whether or not the bacterial strain contains an antibiotic-resistance gene. Additionally, methods provided herein also allow using the data to differentiate between bacteria that may contain different antibiotic-resistance genes. Overall, methods provided herein focus on the use of intrinsic fluorescence, to: 1) differentiate between different types of bacteria (i.e. differentiate between different bacterial species); 2) differentiate between same bacterial species containing different antibiotic-resistance genes; and 3) differentiate between bacterial species that carry an antibiotic-resistance gene from those bacterial species that do not carry an antibiotic-resistance gene. Additionally, methods provided herein allow for analysis of various types of collected suspect samples.

Antimicrobial (i.e., antibacterial) resistance occurs when a microbe (i.e., bacteria and/or bacterial strain) acquires a genetic mutation, either spontaneously or by gene transfer, rendering it resistant to the effect of one or more antibacterial agents, i.e., antibiotics. Drug-resistant organisms may acquire resistance to first-line antibiotics, necessitating the use of a second-line agent to which the microbe is sensitive. In the case of some bacterial strains that have gained resistance to multiple drugs, resistance to second- and even third-line antibiotics is sequentially acquired.

Resistance may take the form of a spontaneous or induced genetic mutation, or the acquisition of resistance genes from other bacterial species by horizontal gene transfer via conjugation, transduction, or transformation. Many antibiotic-resistance genes reside on transmissible plasmids facilitating their transfer. Antibiotic-resistance plasmids frequently contain genes conferring resistance to several different antibiotics.

The increasing rates of antibiotic-resistant bacterial infections seen in clinical practice stems from antibiotic use both within human and veterinary medicine. Any use of antibiotics can increase an evolutionary selective pressure in a population of bacteria, allowing resistant bacteria to thrive and non-resistant bacteria to die off. As resistance to antibiotics becomes more common, a greater need for alternative treatments arise. Antibiotic-resistance poses a grave and growing global problem to public health. With an increasing number of bacterial strains having resistance to antibiotics, individuals who require medicinal help are unable to acquire the proper treatment they require.

Therefore, it is an object of the present invention to provide a quick, rapid method for identifying bacterial strains that contain antibiotic-resistance genes. More so, the identification of what type, or types, of antibiotic resistance the bacteria strain contains is necessary. Identification of bacterial strains containing antibiotic-resistance genes would greatly aid in the development of drug design and treatment regimens.

Description of Related Art

In general, current-day practice for identifying, isolating, and differentiating bacterial strains with and without antibiotic-resistance genes often involves a complex and lengthy process in microbiology labs. In the current processes, biological samples containing bacteria are first accepted into the lab. In one process, the biological samples are then streaked, using a sterilized loop, on agar plates containing a nutritionally-rich medium (for example, lysogeny broth or any other suitable broth). This agar plate contains spots that have been treated with an antibiotic. Once the specimen has been streaked on the plate, the agar plate is placed into a dedicated incubator for a minimum of 12 hours. The agar plates are then periodically checked for bacterial colony growth. As would be appreciated by one of ordinary skill in the art, if the biological sample contains bacteria, then bacterial colony growth is expected on the spots not containing the antibiotic. If the bacteria has not acquired an antibiotic-resistance gene, growth on the spots containing the antibiotic is not expected. However, if the bacterial strain has acquired an antibiotic-resistance gene, colony growth will occur on the spots that have been treated with the antibiotic. See for example, commonly owned U.S. Patent Application Publication No. 2008/0220465.

In another process, biological samples, upon collection, are sorted, labeled, and then inoculated into glass, round-bottom, test-tubes containing blood agar medium, or any other suitable nutritionally-rich growth medium (e.g., lysogeny broth), using a sterilized loop. The specimens are then inserted into a dedicated incubator for a 12- to 24-hour period. The samples are then observed and screened for positive (i.e., containing bacteria) and negative cultures (i.e., not containing bacteria). Samples that appear to contain positive cultures are processed in order to isolate and suspend the bacteria in a biochemical fluid. This process involves suspension, dilution, vortexing, and turbidity measurements resulting in biochemical waste products. The cultures are then subjected to a species identification and antibiotics susceptibility tests, which exposes the bacterial suspensions to multiple reagents. After another 6- to 24-hour incubation period, the findings are interpreted and reported by lab technicians. This entire process generally takes at least 11, or more, steps and at least 50 hours to obtain specimen results and the process is labor intensive.

Other processes to differentiate and identify between bacterial species and/or strains involves various types of nucleic acid sequencing methods. Briefly, DNA sequencing is the process of determining the precise order of nucleotides within a DNA molecule. It includes any method or technology that is used to determine the order of the four bases—adenine, guanine, cytosine, and thymine—in a strand of DNA. In these methods, once a biological sample is obtained, the bacteria contained in the biological sample needs to first be amplified. In other words, the biological sample is first collected, it is then used to inoculate a suitable bacterial growth medium (e.g., blood growth medium or lysogeny broth). The inoculated sample is then grown at appropriate conditions for 12-24 hours. Upon growth, bacterial cells are pelleted from the culture medium, lysed, and processed to extract the bacterial DNA. Bacterial DNA is then cleaned, purified, and placed in a DNA sequencer. The growth of the bacteria and isolation of the bacterial DNA not only requires reagents but also produces bio-waste material, and is additionally a timely process. Additionally, nucleic sequencing methods require the use of primer sequences. A primer is a strand of short nucleic acid sequences (generally about 10 base pairs) that serves as a starting point for DNA synthesis. It is required for DNA replication because the enzymes that catalyze this process, DNA polymerases, can only add new nucleotides to an existing strand of DNA. By requiring primer sequences, this method additionally requires some minimal knowledge of the type of bacterial strain. Sequencing, as indicated, can additionally be time consuming and expensive.

In general, current-day practice for identifying, isolating, and differentiating bacterial strains with and without antibiotic-resistance genes, in a typical microbiology lab, is laborious and is a time-consuming process.

SUMMARY OF THE INVENTION

The increasing number of bacterial strains having resistance to antibiotic drugs has proven problematic for the above-mentioned reasons.

Provided herein are methods for detecting bacterial strains containing resistance to antibiotic drugs. Additionally, this invention relates to methods that allow for the differentiation between bacteria containing different antibiotic-resistance genes. More specifically, methods describing the use of optical analyzers, to identify and differentiate between different bacterial strains are described. As indicated, other suitable optical analyzer systems can be used. The POCARED® P-1000® system is an automated rapid platform that employs intrinsic fluorescence, optical data analysis, and artificial intelligence (for example, through use of chemometric techniques) methods to analyze multi-dimensional optical characteristics of microorganisms. As discussed below, optical data obtained allows differentiation between bacterial strains having or not having an antibiotic-resistance gene and, additionally, between bacterial strains containing different antibiotic-resistance genes. Several benefits are associated with the herein provided methods. These methods eliminate the need for reagents (i.e., reagents that would typically be required in the processing of biological samples), likewise eliminating the generation of bio-waste material, and methods are overall quick, rapid, efficient, and accurate.

Provided is a method for processing a sample, containing one or more bacterial strains, in preparation for identifying and differentiating the bacterial strains, in the sample, carrying one or more antibiotic-resistance genes from those that do not have the one or more antibiotic-resistance genes, wherein the steps include: a) providing the sample that has one or more bacterial strains; b) exciting with a light source the sample that has one or more bacterial strains with a plurality of wavelengths; c) measuring light emission data from step b) and obtaining an excitation emission matrix of the sample; and d) analyzing the excitation emission matrix to determine presence or absence of one or more antibiotic-resistance genes.

Additionally, in one non-limiting embodiment, the sample is a concentrated bacterial sample.

In another one non-limiting embodiment, the sample is a biological sample.

Provided in a non-limiting example, the biological sample is processed to generate a concentrated bacterial sample. For instance, the concentrated bacterial sample is generated by centrifugation. In a non-limiting embodiment, the concentrated bacterial sample is then reconstituted in a saline solution.

In another non-limiting example, the concentrated bacterial sample is generated by filtration. Further, the concentrated bacterial sample is eluted from the filter, thereby producing an eluted, concentrated bacterial sample. The concentrated bacterial sample may be eluted from the filter by using an effervescent solution.

A non-limiting example of the present invention may include the step of obtaining an excitation emission matrix by exciting the sample with multiple different wavelengths, and collecting and detecting fluorescent emissions. Further, the fluorescent emissions may be directed into a spectrophotometer to produce an excitation emission matrix. Additionally, the excitation emission matrix is analyzed using a chemometric technique.

The light source of the present invention may be a UV light source. Further, the light source may have a wavelength or wavelengths in the range of 200 nm to 800 nm, such as 260 nm 270 nm, 275 nm, 280 nm, and 285 nm.

Further, the light emission is fluorescence. Additionally, the light emission may have electromagnetic radiation emissions centered at wavelengths ranging from 200 nm to 800 nm, such as at 230 nm, 260 nm, and 280 nm, but also at 300 nm-420 nm.

Suitable and exemplary excitation and emission parameters are discussed in detail in commonly owned U.S. Patent Application Publication Nos. 2007/0037135 and 2012/0196271, both of which are incorporated herein by reference.

Additionally provided is a method for processing a sample, containing one or more bacterial strains, in preparation for identifying and differentiating the bacterial strains, in the sample, carrying one or more antibiotic-resistance genes from those that do not contain one or more antibiotic-resistance genes, wherein the steps include: a) providing the sample that has one or more bacterial strains; b) exciting the sample that has one or more bacterial strains with a light source that has a wavelength range of 200 nm to 800 nm; c) measuring light emission data having a wavelength range of 200 nm to 800 nm from step b) and obtaining an excitation emission matrix of the sample; and d) analyzing the excitation emission matrix to determine presence or absence of one or more antibiotic-resistance genes.

Alternatively provided is a method for processing a sample, containing one or more bacterial strains, in preparation for identifying and differentiating the bacterial strains, in the sample, carrying one or more antibiotic-resistance genes from those that do not contain one or more antibiotic-resistance genes, wherein the steps include: a) providing the sample that has one or more bacterial strains; b) exciting the sample that has one or more bacterial strains with a UV light with five different wavelengths; c) measuring light emission data from step b) and obtaining an excitation emission matrix of the sample; and d) analyzing the excitation emission matrix to determine presence or absence of one or more antibiotic-resistance genes. Additionally, provided by this method, is wherein the analysis of the excitation emission matrix is by a chemometric technique, and further wherein wherein the light emission is fluorescence.

Additionally provided herein, is a related method for identifying the type, i.e., differentiating between bacterial strains and quantifying the bacterial strains in a biological sample.

The optical analyzer system that is herein described, entails an automated rapid system that employs intrinsic fluorescence, optical data analysis, and artificial intelligence methods to analyze multi-dimensional optical characteristics of microorganisms. It captures the emitted light from the interaction between photons and biomolecules to detect a pathogen's unique optical properties. Optical data that is obtained from the system is then analyzed by chemometric techniques, allowing for the determination and understanding of the type of pathogen and additionally specific characteristics of the pathogen.

BRIEF DESCRIPTION OF THE DRAWING

FIG. 1 is an exemplary illustration of the herein provided method. Briefly, concentrated samples are excited at various wavelengths, their emissions are collected, a spectrophotometer measures the emissions, the emissions are analyzed to produce an excitation emission matrix, and the excitation emission matrix is then used to analyze the unknown sample against known samples through chemometric techniques.

DETAILED DESCRIPTION OF THE INVENTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates, and grammatical variants of those words or phrases.

As used herein, the terms "comprising", "comprise" or, "comprised", and variations thereof, are meant to be open ended. The terms "a" and "an" refer to one or more.

As used herein, the term "patient" or "subject" refers to members of the animal kingdom including, but not limited to, human beings and "mammal" refers to all mammals, including, but not limited to, human beings.

As used herein, the term "sample" or "specimen" or "biological sample/specimen" refers to any material that is submitted to test for the presence of a bacterial strain having an antibiotic-resistance gene. For example, "samples" or "specimens" or "biological sample/specimen" include, but are not limited to, blood, urine, and/or periodontal/oral fluids. "Sample" or "specimen" can additionally refer to samples that have been semi-prepared, in other words, bacterial cultures, such as those grown in suitable growth mediums (e.g., bacterial colony isolates from blood agar plates or bacterial colonies growth in lysogeny broth).

As used herein, the terms: "bacteria" (bacterial or bacterium) and "microbe" (microbial) refer to the same thing.

That is, they refer to single-cell, prokaryotic, micro-organisms, they are small, usually rod-shaped, and may be disease causing. Bacteria-causing diseases are typically treated with antibiotics. Additionally, "bacterial strain" or "bacterial isolates," refer to the same thing. That is, a strain/isolate is a genetic variant, or subtype, of a bacterium. In other words, one type of bacterial species may contain several different strains. The strains differ based on genetic mutations, such as through acquisition of additional genes, such as antibiotic-resistance genes, etc. These terms would be understood by a person of ordinary skill in the art.

Bacteria are grown, that is, cultured, by spreading the bacteria onto the surface of an agar plate (agar contained within a petri dish). This agar is gel-like and contains all the food and nutrients that the bacteria need to grow. As the bacteria consume the nutrients, they begin to grow and multiply. This generates thousands to millions to billions of cells that begin to pile up, becoming visible to the naked eye. This pile of cells originates from one cell and is called a bacterial colony. Culturing (growth) of bacterial cells may also occur by inoculating a liquid of nutritionally-rich growth medium. A nutritionally-rich growth medium is one that contains all the food and nutrients that the bacteria need to grow. An agar plate or liquid growth medium that has been inoculated with an unknown sample is said to be a positive culture if the presence of bacteria is detected or if not, is referred to as a negative culture.

As indicated, bacteria can gain antibiotic resistance through selective pressures, such as through treatment with an antibiotic. That is, because of this resistance, treatment with a specific antibiotic does not result in the killing of the bacteria. This antibiotic resistance can result because the bacteria has acquired an antibiotic-resistance gene. An antibiotic-resistance gene is one which causes an antibiotic that use to be effective in treating or preventing an infection caused by that bacteria to become ineffective.

Resistance may occur in many ways. For example, resistance may take the form of a spontaneous or induced genetic mutation, or the acquisition of resistance genes from other bacterial species by horizontal gene transfer via conjugation, transduction, or transformation. Resistance can happen spontaneously, owing to random mutations, to a buildup of resistance over time, or the misuse of antibiotics or antimicrobials. Horizontal gene transfer refers to the transfer of genes between two or more bacterium in a manner other than traditional reproduction. Transduction is when a virus infects a bacterium and some bacterial DNA becomes entrapped in the viral capsid; this virus infects another bacterium, which causes the transfer of DNA of the previous bacterium. Transformation refers to bacterium taking DNA from its environment, perhaps because of selective (evolutionary) pressures. Additionally, many antibiotic-resistance genes reside on transmissible plasmids facilitating their transfer, permitting easy acquisition. These mechanisms, as well as any other mechanisms of gaining antibiotic resistance, are well known in art.

Provided herein is a method for processing a biological sample in preparation for: identifying the type of bacterial micro-organism and quantifying it in a biological sample; identifying; and differentiating bacterial strains containing or not containing an antibiotic-resistance gene; finally, identifying and differentiating bacteria containing different resistance genes in the biological sample. The steps include: obtaining the biological sample; concentrating the bacteria in the biological sample; either reconstituting the concentrated bacterial sample in a saline solution or filtering the biological sample to obtain the concentrated bacterial sample and eluting the bacterial sample from the filter with a suitable solution (i.e., one that is effervescent, for example); transferring the concentrated bacterial of the previous step into an optical cup or cuvette for analysis; subjecting the optical cup or cuvette to an optical analysis, wherein the optical analysis includes an optical analyzer having optics, and wherein the optical analysis includes exciting the fluid sample with a plurality of different wavelengths, collecting, and detecting the fluorescent emissions; directing the fluorescent emissions into a spectrophotometer; and obtaining an excitation emission matrix of the bacterial sample and analyzing the excitation emission matrix of the sample using one or more chemometric techniques to determine the presence or absence of an antibiotic-resistance gene.

FIG. 1 is an exemplary illustration of the herein provided method. FIG. 1 is a depiction of the entire sample processor as described herein. More specifically, the sample processor of the present invention allows for the following method: 1) processing of a biological sample to generate a concentrated bacterial sample; 2) an optical analyzer that has capability of exciting the bacterial sample at various wavelengths (via the excitation unit of the optical analyzer); 3) mechanisms that permit the emissions to be directed and reflected back to a collection unit; 4) a spectrophotometer that can receive and measure the emissions produced; 5) an analytic system that is capable of obtaining the emission data, and then analyzing the data to produce an excitation emission matrix (or matrices); and 6) an analytic system that uses chemometric techniques to draw conclusions about the unknown samples.

The herein described method utilizes intrinsic fluorescence properties of bacterial strains to identify and differentiate not only between bacterial species but also between a particular bacterial species that has or does not have an antibiotic-resistance gene. Additionally, this invention relates to methods that allow for the differentiation between bacteria with different antibiotic-resistance genes.

The methods described herein can be easily and rapidly performed through the automated platform provided by the POCARED® P-1000® system. The method of detection, that is, the measuring of intrinsic fluorescence of the sample, can additionally be performed in any other suitable way. More specifically, the following commonly owned United States patents and patent application publications describe the herein described system: U.S. Pat. Nos. 8,309,897, 8,519,358, 8,804,114 and 8,808,649, and additionally, U.S. Patent Application Publication Nos. 2011/0093207, 2012/0196271, 2014/0246389, and 2015/0152467, each of which are herein incorporated by reference.

The herein provided methods streamline currently used methods for obtaining, processing, and analyzing specimen results. Methods provided are environmentally friendly, enable rapid diagnosis, results are consistent, no reagents are needed, and there is a multifunctional diagnosis.

Biological samples are first collected, not limited to but including from a bacterial culture, bacterial blood agar plate, or from a patient, through standard procedures that are well known in the art. These biological samples are then processed in order to obtain a concentrated bacterial sample. Suitable systems for obtaining a concentrated bacterial sample are discussed in the commonly owned U.S. patents and patent application publications listed above.

In general, biological samples may be concentrated by centrifugation, such as described, for example, in U.S. Pat. No. 8,804,114, or by running the sample through a filter system, such as described, for example, in U.S. Patent Application Publication No. 2014/0246389. Briefly, samples can be centrifuged to obtain a pellet of bacterial cells. This pellet can then be reconstituted in an optically clear solution, such as a suitable saline solution. For example, a buffered saline solution, such as, but not limited to, phosphate buffered saline (PBS).

Additionally, use of a filter or membrane having a small pore size can be used to capture bacterial cells. The bacterial cells can then be eluted from the filter or membrane. Such an arrangement is described in U.S. Patent Application Publication No. 2014/0246389. Generally, the filter element is preferably a polycarbonate-type filter, or any suitable equivalent, which is a surface filter and may have pore sizes ranging from 0.1 to 10 microns wide. The filter arrangement, for example, is as follows: a top element and a bottom element and a filter element therebetween captures oversized particles on the upper surface of the filter element and tangentially rinses these particles using an elution fluid to provide a concentration of particles in a relatively low volume of fluid for further analysis. In an intermediate step, the particles captured by the filter may be rinsed with a rinsing fluid, such as water, to pass additional undersized particles through the filter, thereby providing a purer sample. Additionally, in order to improve efficiency, the filter system may include check valves, which may be used for passageways with one-way flow. Additionally, a configuration of three-way stopcocks may also be utilized in the filter system. Finally, a sandwich arrangement of the filter system is possible, wherein a single bottom element is sandwiched between two opposing top elements.

As is known in the prior art, the elution fluid may be, and preferably is, effervescent and may contain a foaming agent, for example, but not limited to, TWEEN, or any other suitable equivalent. Further, the elution fluid may be a saline solution, such as a buffered saline solution (e.g., phosphate buffered saline).

These concentration means require minimal to no use of reagents and, more importantly, the processes, as described herein, do not result in the production of bio-waste materials.

Suitable suspensions of concentrated bacteria have a concentration of at least $10^7$ CFU/ml or $10^8$ CFU/ml bacteria (0.5 McFarland).

Prepared, concentrated bacterial specimens are then transferred into optical cups or cuvettes, which are then subsequently inserted into an optical analyzer which analyzes the specimens. Suitable cuvettes and/or optical cups are described in the above-referenced U.S. patents and patent application publications.

Herein, optical analyzers refer to systems capable of exciting a fluid sample with a plurality of different wavelengths (via the excitation module unit), capturing the emitted light (via the optical collection unit) from the interaction between photons and molecules of the fluid sample an excitation emission matrix is produced, and processing and analysing the excitation emission matrix using chemometric analysis techniques to determine what specific characteristics (such as the presence of an antibiotic-resistance gene) based on the optical characteristics of the fluid sample.

Briefly and as discussed in the U.S. patents and patent application publications mentioned above (see for example, U.S. Patent Application Publication No. 2012/0196271), a suitable optical analyzer contains: an optics system; a thermal control; and a drawer which has a rotatable table for receiving, supporting and rotating a magazine containing a plurality of disposable cartridges with optical cups or cuvettes which contain samples to be analyzed. The optical analyzer also contains a bar code reader for inventorying the samples and a level sensor that verifies that each optical cup or cuvette contains the correct volume of processed sample. When the drawer with the magazine is inserted into the optical analyzer, the drive mechanism for the rotatable table supporting the magazine rotates and registers the magazine relative to the bar code reader and then rotates and registers the magazine relative to the optics system. The optics system includes: an excitation module unit (laser unit) or alternatively LEDs of differing wave lengths; an optical collection unit (sensor unit); and a spectrophotometer. The temperature of each cup or cuvette is decreased to a temperature which will slow the metabolism of the bacteria in the samples while increasing the fluorescence signal. A thermal control cools a large thermal mass, which is located on the rotatable table underneath the magazine containing the disposable cartridges with sample cups or cuvettes. An infrared temperature sensor detects and monitors the temperature of each sample.

More specifically, the optics system may contain three or more separate units, that is, at minimum, the optics system includes: an excitation unit; an optical collection unit; and a spectrophotometer. Excitation will be provided by a ultraviolet (UV) light source (also referred to as light or light source), which preferably will be a LED (light emitting diode). Preferably, a series of five (or more) LED modules provide an excitation unit and will sequentially provide excitation signals to each sample cup or cuvette at five (or more) different excitation wavelengths, which will be applied to each sample cup or cuvette in the same order. Fluorescent emissions are reflected back in an upward direction to the optical collection unit. Optical elements are utilized to gather and direct the fluorescent emissions into the spectrophotometer for measurement. Measurements by the spectrophotometer are analyzed and an excitation emission matrix is generated.

The optical analyzer analyzes and generates the complete results, based on intrinsic fluorescence and chemometric analyzes, providing the operator with information about the types of bacterial strains present and whether or not these bacteria contain an antibiotic-resistance gene. The system does not require a sophisticated operator and gives rapid results. The system increases efficiency, improves workload, saves time and money, and is easy to operate. The sample preparation can be performed in parallel with the specimen analysis process and from 1 to 50 specimens can be analyzed simultaneously.

By intrinsic fluorescence it is meant that live bacteria contain a variety of intracellular biomolecules that have specific excitation and emission wavelength spectra. Fluorescence spectroscopy has been extensively exploited for studies of molecular structure and function in chemistry and biochemistry. However, its effectiveness in microbial identification and characterization has only been recently recognized in the last two decades. Live bacteria own numerous intracellular biological molecules associated with energy-yielding reactions. The fluorescent characteristics of these endogenous molecules at specific excitation and emission wavelengths make them very attractive probes for biological detection and characterization. These endogenous fluorophores include protein tryptophans, other amino acids (tyrosine and phenylalanine), nucleic acids, and co-enzymes. Their excitation maxima lie in the range of 250-450 nm (spanning the UV/VIS spectral range), such as 260 nm, 270 nm, 275 nm, 280 nm, and 285 nm, whereas their emission maxima lie in the range of 280-540 nm, and preferably 300-420 nm (spanning the UV/VIS spectral range).

As indicated, methods herein involve simultaneous collection of fluorescence data over a wide range of different excitation and emission wavelengths. The resulting excitation emission matrix (EEM) provides a total intensity profile of the sample over the range of excitation and emission wavelengths scanned.

According to the present invention, various datasets may be generated. These datasets are generated based on excitation emission matrices for various bacterial strains. Specifically, datasets are generated for various "normal" bacterial strains, that is, bacterial strains without any antibiotic-resistance genes. Datasets are additionally generated for bacterial strains that have one or more antibiotic-resistance genes. The datasets are necessary for chemometric analysis techniques, as discussed below. Specifically, chemometric analysis techniques compare excitation emission matrices of unknown samples with the known excitation emission matrices, as complied in the aforementioned datasets, to determine what the unknown samples are.

Chemometric analysis are multivariate analyzes that involves the use of mathematical and statistical methods to design or select optimal procedures and experiments, and to provide maximum chemical information by analyzing chemical data. The analysis of absorption or emission data identifies individual performance indicators and is used to calculate an estimate of their concentration and/or presence in an aqueous solution. Chemometric techniques are well known in the art and any suitable chemometric analysis may be used. Suitable techniques include, but are not limited, to the following: partial least squares (PLS); partial least squares-discriminant analysis (PLS-DA); extended partial least squares analysis (EPLS); orthogonal partial least squares discriminant analysis (OPLS-DA); and linear discriminant analysis (LDA).

PLS analysis determines linear regression models by projecting predicted variables and the observable variables to a new space. PLS-DA is a variant used when one dataset is categorical. EPLS is another form of PLS.

OPLS-DA is a supervised multiple regression analysis for identification of discrimination between different datasets. In OPLS, continuous variable data is separated into predictive and uncorrelated information. This leads to improved diagnostics, as well as more easily interpreted visualization. OPLS-DA may be applied when working with discrete variables, as in classification and biomarker studies.

LDA is a method used in statistics and is a method of pattern recognition and machine learning to find a linear combination of features that characterizes or separates two or more classes of objects or events. The resulting combination may be used as a linear classifier, or, more commonly, for dimensionality reduction before later classification.

The chemometric analysis techniques described above are well known in the art and as indicated, are merely included herein as exemplary chemometric analysis techniques. As such, any suitable chemometric analysis technique may be used.

The sample processor of the invention streamlines the current practice for processing biological samples for analysis. The sample processor of the invention is automated, fully compact, self-contained, and does not require any reagents. The sample processor does not require a sophisticated operator and rapidly processes the samples or specimens. The sample processor increases efficiency, improves workload, saves time and money, and is easy to operate. The processing of several samples can be performed in about 20 minutes for a single specimen and up to 1 hour for about 50 specimens. Upon sample preparation, analysis time takes only 10 minutes. Overall, the herein provided methods allow for a quick, efficient method for identifying and characterizing bacteria.

The present invention is more particularly described in the examples that follow, which are intended to be illustrative only.

EXAMPLES

Example 1

The purpose of this study was to use the POCARED® P-1000® system to differentiate isolates of commonly encountered bacteria that contain specific resistance genes from similar isolates that do not harbor the gene. More specifically, the optical analyzer described above was used to differentiate isolates of commonly encountered bacteria that contain specific resistance genes from similar isolates that do not harbor the gene.

Methods: Strains evaluated containing antibiotic resistant genes included: *Acinetobacter baumannii* (AB) with $bla_{OXA}$ (n=2), *Escherichia coli* (EC) with $bla_{NDM}$ (n=3), *Klebsiella pneumoniae* (KP) with $bla_{NDM}$ (n=5), EC with $bla_{KPC}$ (n=1), KP with $bla_{KPC}$ (n=5), *Enterococcus faecalis* (EF) with vanB (n=2), and *Staphylococcus aureus* (SA) with mecA (n=4). Control strains without resistance genes included: 1 each of AB, EC, EF, KP, and SA. All isolates were obtained from American Type Culture Collection (ATCC). Bacterial suspensions, in phosphate buffered saline (PBS), containing $10^8$ CFU/ml (0.5 McFarland) were analyzed using the POCARED® P-1000® system which measures excitation emission matrix (EEM) of the sample. Specifically, five excitation wavelengths were used (260 nm, 270 nm, 275 nm, 280 nm, and 285 nm). Emission data wavelengths ranged from 300 nm to 420 nm. The EEMs were processed using a chemometric technique (specifically the PLS-DA method) and for each isolate tested 30 times, a prediction was generated. The accuracy for the prediction was calculated as the total number of correct predications divided by the total number of measurements.

Results: The accuracy for detecting isolates containing a specific resistance gene was 98%, 96%, 95%, 97%, and 95% for AB, EC, EF, KP, and SA, respectively. The accuracy for differentiating bacteria containing $bla_{KPC}$ or $bla_{NDM}$ in EC and KP was 99% and 98%, respectively.

Conclusion: Using chemometric analysis of EEMs which is the basis of the POCARED® P-1000® system, differentiation of bacteria with a resistance gene from bacteria without a resistance gene was possible. In addition, differentiation between bacteria with different resistance genes was possible.

While the present invention has been described in terms of the above examples and detailed description, those of ordinary skill will understand that alterations may be made within the spirit of the invention. Thus, the present invention is capable of many variations in detailed implementation, which may be derived from the description contained herein by a person of ordinary skill in the art.

We claim:

1. A method for processing a sample, comprising one or more bacterial strains, in preparation for identifying and differentiating the bacterial strains, in the sample, carrying one or more antibiotic-resistance genes from those that do not contain one or more antibiotic-resistance genes, wherein the steps comprise, determining the intrinsic fluorescence of the one or more bacterial strains in the sample by:

a) providing a system capable of detecting one and more than one bacterial strain in a single specimen;
b) providing the system of a) with the sample comprising one or more bacterial strains;
c) exciting with an ultra-violet light source the sample comprising one or more bacterial strains with a plurality of wavelengths;
d) measuring light emission data from step c) and obtaining an excitation emission matrix of the sample; and
e) generating control datasets from emission excitation matrices of bacterial strains that do not have one or more antibiotic resistance genes, and classifying the one or more antibiotic-resistance genes of the one or more bacterial strains in the sample by using chemometric analysis techniques, thereby differentiating the one or more bacterial strains in the sample carrying one or more antibiotic-resistance genes from those that do not contain one or more antibiotic-resistance genes, wherein the one or more bacterial stains comprised in the sample are unbound.

2. The method of claim 1, wherein the sample is a concentrated bacterial sample.

3. The method of claim 1, wherein the sample is a biological sample.

4. The method of claim 3, wherein the biological sample is processed to generate a concentrated bacterial sample.

5. The method of claim 4, wherein the concentrated bacterial sample is generated by centrifugation.

6. The method of claim 5, wherein the concentrated bacterial sample is reconstituted in a saline solution.

7. The method of claim 4, wherein the concentrated bacterial sample is generated by filtration.

8. The method of claim 7, wherein the concentrated bacterial sample is eluted from the filter, thereby producing an eluted, concentrated bacterial sample.

9. The method of claim 8, wherein the concentrated bacterial sample is eluted by using an effervescent solution.

10. The method of claim 1, wherein the step of obtaining an excitation emission matrix comprises, exciting the sample with multiple different wavelengths, and collecting and detecting fluorescent emissions.

11. The method of claim 1, further comprising directing the light emissions into a spectrophotometer to produce the excitation emission matrix.

12. The method of claim 1, wherein the light source has a wavelength range of 200 nm to 800 nm.

13. The method of claim 1 wherein the light emission has a wavelength range of 200 nm to 800 nm.

14. A method for processing a sample, comprising one or more bacterial strains, in preparation for identifying and differentiating the bacterial strains, in the sample, carrying one or more antibiotic-resistance genes from those that do not contain one or more antibiotic-resistance genes, wherein the steps comprise, determining the intrinsic fluorescence of the one or more bacterial strains in the sample by:

a) providing a system capable of detecting one and more than one bacterial strain in a single specimen;
b) providing the system of a) with the sample comprising one or more bacterial strains;
c) exciting the sample comprising one or more bacterial strains with a light source that has a wavelength range of 200 nm to 800 nm;
d) measuring light emission data having a wavelength range of 200 nm to 800 nm from step c) and obtaining an excitation emission matrix of the sample; and
e) generating control datasets from emission excitation matrices of bacterial strains that do not have one or more antibiotic resistance genes, and classifying the one or more antibiotic-resistance genes of the one or more bacterial strains in the sample by using chemometric analysis techniques, thereby differentiating the one or more bacterial strains in the sample carrying one or more antibiotic-resistance genes from those that do not contain one or more antibiotic-resistance genes, wherein the one or more bacterial stains comprised in the sample are unbound.

15. A method for processing a sample, comprising one or more bacterial strains, in preparation for identifying and differentiating the bacterial strains, in the sample, carrying one or more antibiotic-resistance genes from those that do not contain one or more antibiotic-resistance genes, wherein the steps comprise, determining the intrinsic fluorescence of the one or more bacterial strains in the sample by:

a) providing a system capable of detecting one and more than one bacterial strain in a single specimen;
b) providing the system of a) with the sample comprising one or more bacterial strains;
c) exciting the sample comprising one or more bacterial strains with a UV light with five different wavelengths;
d) measuring light emission data from step c) and obtaining an excitation emission matrix of the sample; and
e) generating control datasets from emission excitation matrices of bacterial strains that do not have one or more antibiotic resistance genes, and classifying the one or more antibiotic-resistance genes of the one or more bacterial strains in the sample by using chemometric analysis techniques, thereby differentiating the one or more bacterial strains in the sample carrying one or more antibiotic-resistance genes from those that do not contain one or more antibiotic-resistance genes, wherein the one or more bacterial stains comprised in the sample are unbound.

16. A method for processing a sample, comprising one or more bacterial strains, in preparation for identifying and differentiating the bacterial strains, in the sample, carrying one or more antibiotic-resistance genes from those that contain one or more different antibiotic-resistance genes, wherein the steps comprise, determining the intrinsic fluorescence of the one or more bacterial strains in the sample by:

a) providing a system capable of detecting one and more than one bacterial strain in a single specimen;
b) providing the system of a) with the sample comprising one or more bacterial strains;
c) exciting with an ultra-violet light source the sample comprising one or more bacterial strains with a plurality of wavelengths;
d) measuring light emission data from step c) and obtaining an excitation emission matrix of the sample; and
e) generating control datasets from emission excitation matrices of bacterial strains that have one or more antibiotic resistance genes, and classifying the one or more antibiotic-resistance genes of the one or more bacterial strains in the sample by using chemometric analysis techniques, thereby differentiating the one or more bacterial strains in the sample carrying one or more antibiotic-resistance genes from those that have one or more antibiotic-resistance genes, wherein the one or more bacterial stains comprised in the sample are unbound.

17. A method for processing a sample, comprising one or more bacterial strains, in preparation for identifying and differentiating the bacterial strains, in the sample, carrying one or more antibiotic-resistance genes from those that contain one or more different antibiotic-resistance genes, wherein the steps comprise, determining the intrinsic fluorescence of the one or more bacterial strains in the sample by:

a) providing a system capable of detecting one and more than one bacterial strain in a single specimen;
b) providing the system of a) with the sample comprising one or more bacterial strains;
c) exciting with an ultra-violet light source the sample comprising one or more bacterial strains with a plurality of wavelengths;
d) measuring light emission data from step c) and obtaining an excitation emission matrix of the sample; and
e) generating control datasets from emission excitation matrices of bacterial strains that have one or more antibiotic resistance genes, and classifying the one or more antibiotic-resistance genes of the one or more bacterial strains in the sample by using chemometric analysis techniques, thereby differentiating the one or more bacterial strains in the sample carrying one or more antibiotic-resistance genes from those that have one or more antibiotic-resistance genes, wherein the method does not comprise a step to separate the one or more bacterial strains from each other.

* * * * *